(12) United States Patent
Akagi et al.

(10) Patent No.: US 10,527,410 B2
(45) Date of Patent: Jan. 7, 2020

(54) SHAPE MEASUREMENT APPARATUS AND SHAPE MEASUREMENT METHOD

(71) Applicant: NIPPON STEEL & SUMITOMO METAL CORPORATION, Tokyo (JP)

(72) Inventors: Toshio Akagi, Tokyo (JP); Yusuke Konno, Tokyo (JP); Atsuhiro Hibi, Tokyo (JP); Nobuhiro Furuya, Tokyo (JP); Takayuki Sonoda, Tokyo (JP); Akihito Nakazaki, Tokyo (JP)

(73) Assignee: NIPPON STEEL CORPORATION, Tokyo (JP)

( * ) Notice: Subject to any disclaimer, the term of this patent is extended or adjusted under 35 U.S.C. 154(b) by 0 days.

(21) Appl. No.: 15/767,081

(22) PCT Filed: Jan. 19, 2017

(86) PCT No.: PCT/JP2017/001720
§ 371 (c)(1),
(2) Date: Apr. 9, 2018

(87) PCT Pub. No.: WO2018/016102
PCT Pub. Date: Jan. 25, 2018

(65) Prior Publication Data
US 2018/0292203 A1  Oct. 11, 2018

(30) Foreign Application Priority Data

Jul. 19, 2016  (JP) .................. 2016-141611

(51) Int. Cl.
*G01B 11/30* (2006.01)
*G01B 11/24* (2006.01)
*G01N 21/892* (2006.01)

(52) U.S. Cl.
CPC .............. *G01B 11/30* (2013.01); *G01B 11/24* (2013.01); *G01N 21/892* (2013.01)

(58) Field of Classification Search
CPC ......... G01B 11/30; G01B 11/25; G01B 11/24; G03F 7/20; G01N 21/88; G01N 21/892;
(Continued)

(56) References Cited

U.S. PATENT DOCUMENTS

| 5,521,692 A | 5/1996 | Bares |
| 2018/0202924 A1* | 7/2018 | Harigaya et al. .... G01N 33/483 |

FOREIGN PATENT DOCUMENTS

| JP | 5-133742 A | 5/1993 |
| JP | 6-201347 A | 7/1994 |

(Continued)

OTHER PUBLICATIONS

International Search Report for PCT/JP2017/001720 dated Apr. 18, 2017.
(Continued)

*Primary Examiner* — Jamil Ahmed
(74) *Attorney, Agent, or Firm* — Birch, Stewart, Kolasch & Birch, LLP

(57) ABSTRACT

[Object] To provide a shape measurement apparatus that is capable of detecting minute roughness irregularity at high speed across the entire width on the entire surface of a measurement object.
[Solution] Provided is a shape measurement apparatus including: a light source configured to irradiate a surface of a moving strip-shaped body with linear light diagonally from an upstream side in a movement direction of the strip-shaped body; a screen configured such that reflected light of the linear light on the surface of the strip-shaped body is projected on the screen; an imaging unit configured to image the reflected light of the linear light projected on the screen; and an arithmetic processing unit configured to acquire surface roughness distribution of the strip-shaped body on the basis of width distribution of a light strip of the
(Continued)

reflected light of the linear light projected on the screen. The angle of incidence of the light source with respect to the strip-shaped body is set in accordance with target surface roughness of the surface of the strip-shaped body.

13 Claims, 13 Drawing Sheets

(58) Field of Classification Search
CPC ........ G01N 21/956; H04N 9/07; H04N 5/225; G01C 9/02
See application file for complete search history.

(56) References Cited

FOREIGN PATENT DOCUMENTS

| | | | |
|---|---|---|---|
| JP | 2004-184397 A | 5/2002 | |
| JP | 2004-184397 A | 7/2004 | |
| JP | 2004184397 A | * 7/2004 | ............ G01B 11/24 |
| JP | 2006-3372 A | 1/2006 | |
| JP | 2009-111230 A | 5/2009 | |
| JP | 2012-008078 A | 1/2012 | |

OTHER PUBLICATIONS

Written Opinion of the International Searching Authority for PCT/JP2017/001720 (PCT/ISA/237) dated Apr. 18, 2017.
JP Decision to Grant a Patent, dated Dec. 19, 2017, issued in Japanese Application No. 2017-559484.
Extended European Search Report dated Oct. 12, 2018, issued in European Patent Application No. 17830624.7.
Korean Office Action dated Dec. 26, 2018, issued in corresponding Korean Patent Application No. 10-2018-7011053.
Korean Office Action, dated Jul. 26, 2019, for corresponding Korean Application No. 10-2018-7011053, with an English translation.
European Office Action, dated Jun. 18, 2019, for corresponding European Application No. 17830624.7.

* cited by examiner

SHAPE MEASUREMENT APPARATUS AND SHAPE MEASUREMENT METHOD

TECHNICAL FIELD

The present invention relates to a shape measurement apparatus and a shape measurement method that measure surface roughness distribution of a strip-shaped body.

BACKGROUND ART

Conventionally, materials whose surface roughness is managed, such as a tin plate, have faced a problem of a partial abnormality in surface roughness caused by abrasion of rolling mill rolls or a difference in the amount of drawing of rolling oil. To detect this partial abnormality, there are needs for measuring surface roughness of a material being managed as a measurement object. As a technique for measuring surface roughness in a noncontact manner, angle-resolved scattering using the degree of scattering of light reflected on a surface (JIS B0681-6 (2014)) is known, and some surface roughness measurement methods applying this principle have been proposed.

For example, Patent Literature 1 discloses a laser type surface roughness measurement apparatus that measures surface roughness of a measurement object according to spread of a diffraction pattern of laser spot light. In addition, Patent Literature 2 discloses a method of projecting a reference pattern on the surface of a rough-surface object, forming an image of fluctuation of a reflected image of the reference pattern, and measuring surface texture of the rough-surface object on the basis of luminance distribution of the fluctuation and magnitude of the fluctuation of the reflected image, which are obtained by analyzing a captured image obtained by imaging the fluctuation of the reflected image.

CITATION LIST

Patent Literature

Patent Literature 1: JP H5-133742A
Patent Literature 2: JP 2006-3372A

SUMMARY OF INVENTION

Technical Problem

However, Patent Literature 1 cannot measure surface roughness at high speed, because surface roughness of the measurement object is measured by performing point scanning. In addition, Patent Literature 2 uses a grid pattern as the reference pattern, and cannot detect roughness irregularity smaller than a grid pitch.

Thus, the present invention has been made in view of the problems mentioned above, and an object of the present invention is to provide a new and improved shape measurement apparatus and a new and improved shape measurement method that are capable of detecting minute roughness irregularity at high speed across the entire width on the entire surface of a measurement object.

Solution to Problem

According to an aspect of the present invention in order to achieve the above-mentioned object, there is provided a shape measurement apparatus including: a light source configured to irradiate a surface of a moving strip-shaped body with linear light at a prescribed angle of incidence from an upstream side or a downstream side in a movement direction of the strip-shaped body; a screen configured such that reflected light of the linear light on the surface of the strip-shaped body is projected on the screen; an imaging unit configured to image the reflected light of the linear light projected on the screen; and an arithmetic processing unit configured to acquire surface roughness distribution of the strip-shaped body on the basis of width distribution of a light strip of the reflected light of the linear light imaged by the imaging unit. The angle of incidence is set in accordance with target surface roughness of the surface of the strip-shaped body.

A spectral half-width of the light source may be 20 nm or more.

In addition, an angle of incidence of the light source is set to be larger for larger target surface roughness of the surface of the strip-shaped body.

The arithmetic processing unit may include an image analysis unit configured to acquire, from luminance distribution of a light strip of reflected light of the strip-shaped body included in a captured image acquired by the imaging unit, width distribution of the light strip, and a surface roughness distribution acquisition unit configured to acquire the surface roughness distribution of the strip-shaped body on the basis of the width distribution of the light strip.

The arithmetic processing unit may further include a determination unit configured to determine whether the surface of the strip-shaped body has the target surface roughness, on the basis of the surface roughness distribution.

According to another aspect of the present invention in order to achieve the above-mentioned object, there is provided a shape measurement method including: a first step of using a light source to irradiate a surface of a moving strip-shaped body with linear light diagonally from an upstream side in a movement direction of the strip-shaped body, and using an imaging unit to image a screen on which reflected light of the linear light on the surface of the strip-shaped body is projected and acquiring a captured image in which a screen image that is reflected light of the strip-shaped body is included, the light source being installed to have an angle of incidence set in accordance with target surface roughness of the surface of the strip-shaped body; and a second step of acquiring surface roughness distribution of the strip-shaped body on the basis of width distribution of a light strip of the reflected light of the linear light projected on the screen.

Advantageous Effects of Invention

As described above, according to the present invention, it is possible to detect minute roughness irregularity at high speed across the entire width on the entire surface of a measurement object.

DESCRIPTION OF EMBODIMENTS

Figure 1:
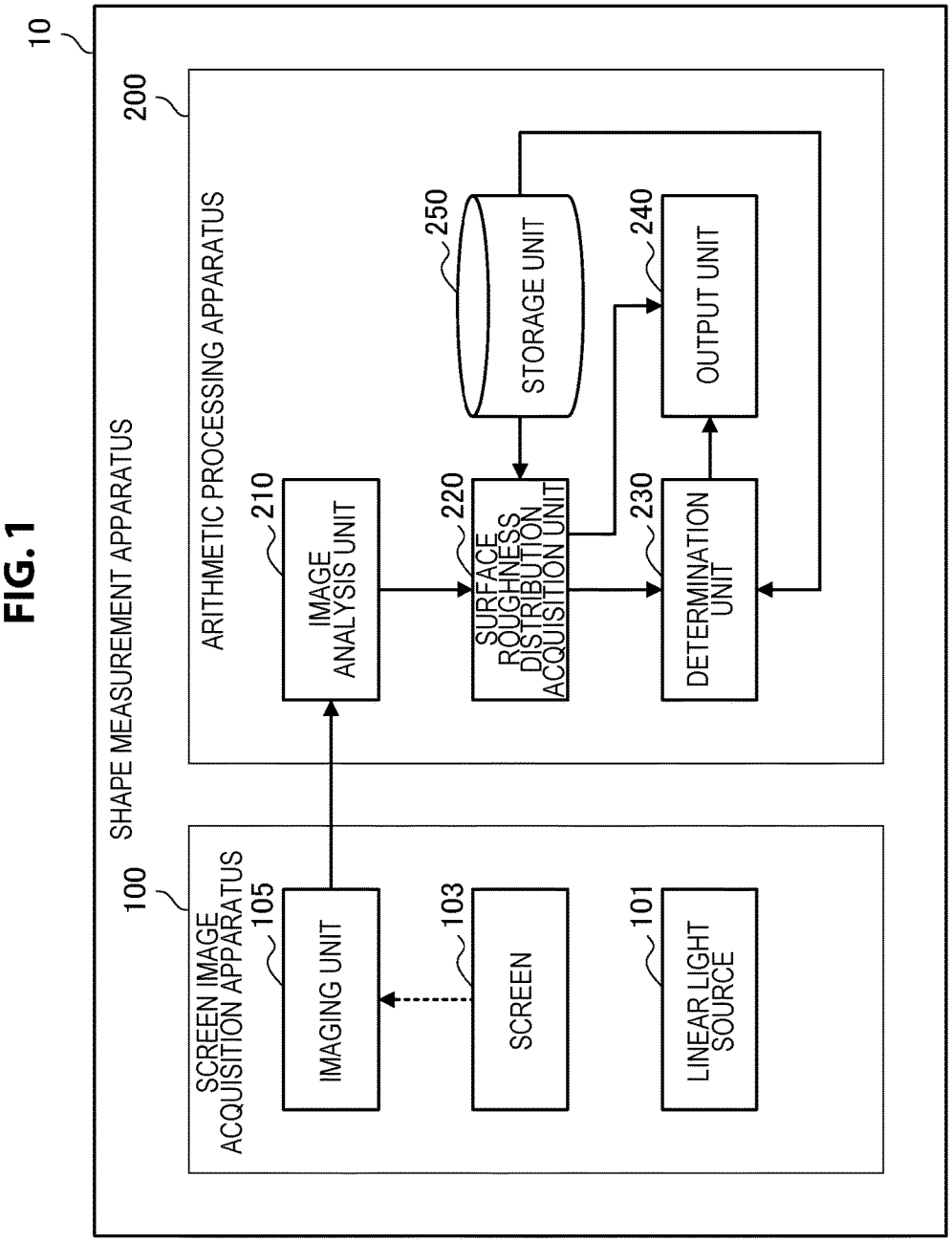
FIG. 1 is a block diagram showing a schematic configuration of a shape measurement apparatus according to an embodiment of the present invention.

Hereinafter, (a) preferred embodiment(s) of the present invention will be described in detail with reference to the appended drawings. In this specification and the appended drawings, structural elements that have substantially the same function and structure are denoted with the same reference numerals, and repeated explanation of these structural elements is omitted.

(1. Schematic Configuration of Shape Measurement Apparatus)

Figure 2:
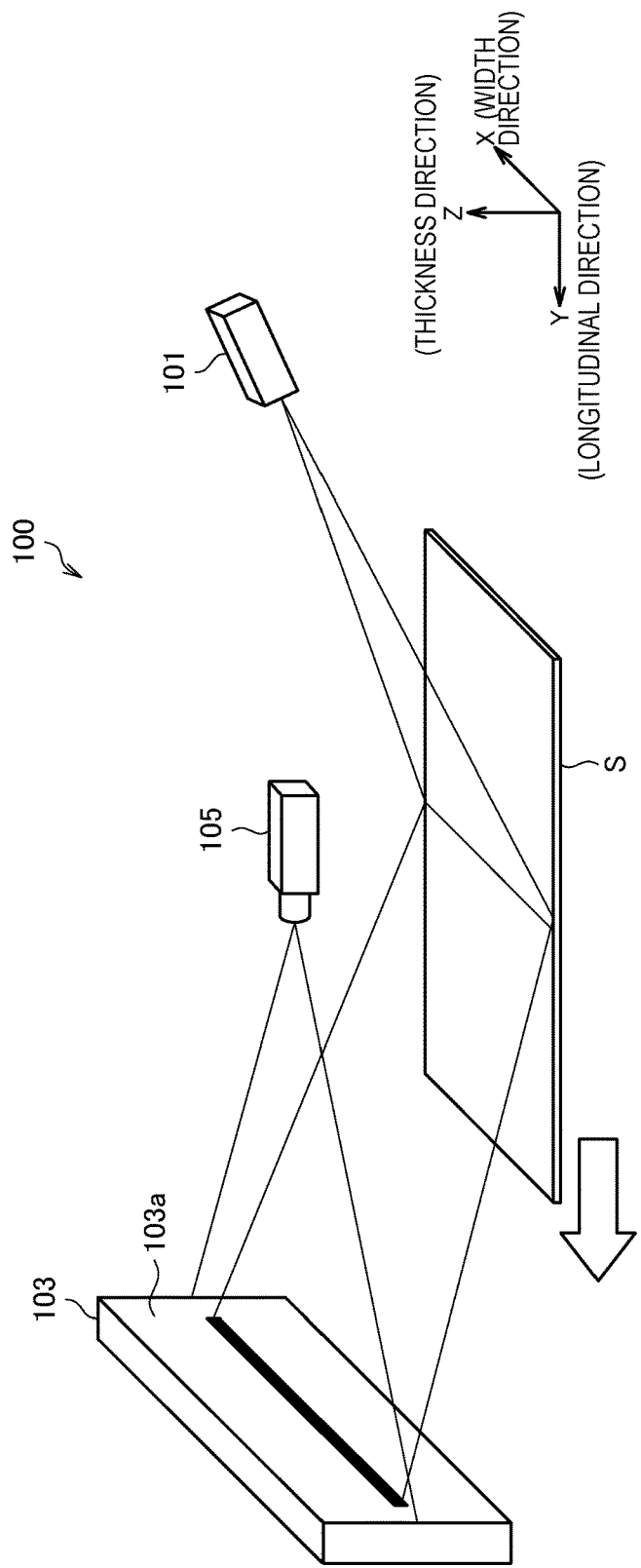
FIG. 2 is an explanatory diagram schematically showing an example of the configuration of a screen image acquisition apparatus of the shape measurement apparatus according to the embodiment.
Figure 3:
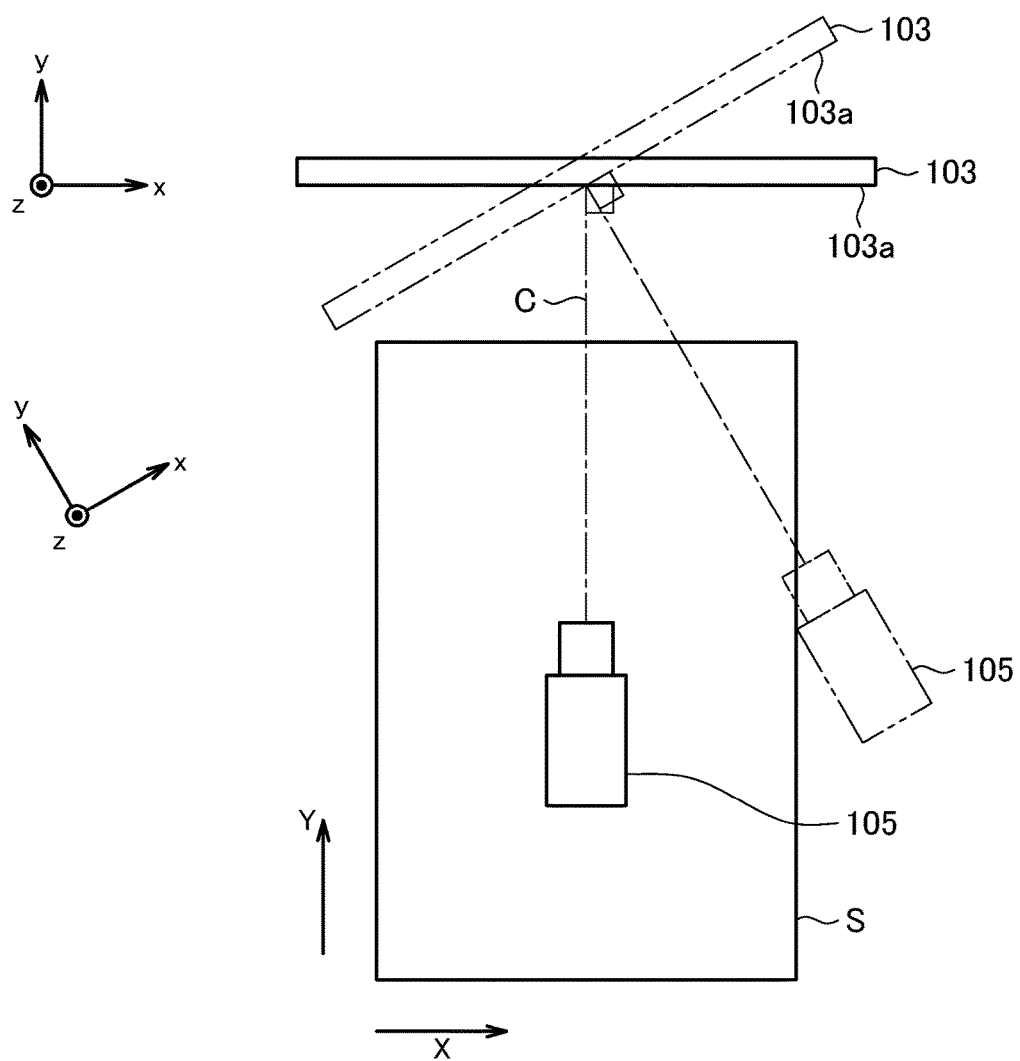
FIG. 3 is a plan view schematically showing a positional relationship between a screen and an imaging unit.
Figure 4:
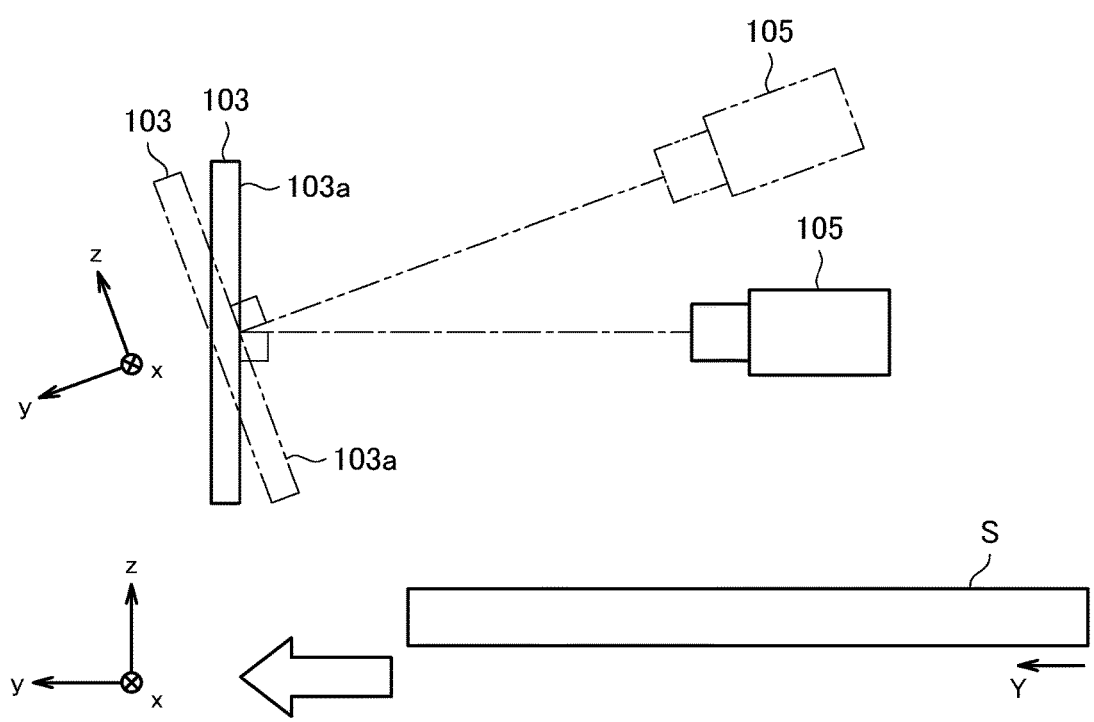
FIG. 4 is a side view schematically showing a positional relationship between the screen and the imaging unit.
Figure 5:
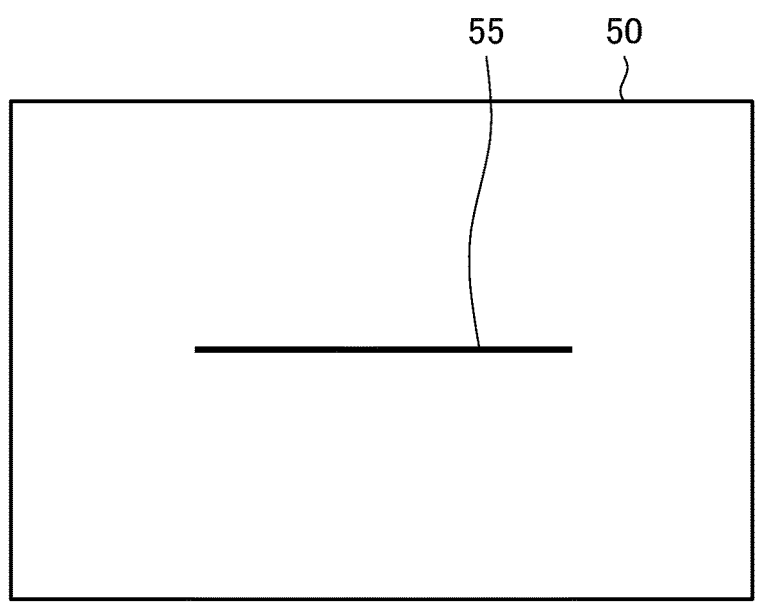
FIG. 5 is an explanatory diagram showing an example of a captured image including a screen image obtained by the imaging unit.

First, a schematic configuration of a shape measurement apparatus 10 according to an embodiment of the present invention is described with reference to FIG. 1 to FIG. 5. FIG. 1 is a block diagram showing a schematic configuration of the shape measurement apparatus 10 according to an embodiment of the present invention. FIG. 2 is an explanatory diagram schematically showing an example of the configuration of a screen image acquisition apparatus 100 of the shape measurement apparatus 10 according to the embodiment. FIG. 3 is a plan view schematically showing a positional relationship between a screen 103 and an imaging unit 105. FIG. 4 is a side view schematically showing a positional relationship between the screen 103 and the imaging unit 105. FIG. 5 is an explanatory diagram showing an example of a captured image 50 including a screen image 55 obtained by the imaging unit.

The shape measurement apparatus 10 according to an embodiment of the present invention is a surface roughness measurement apparatus that applies linear illumination light to the surface of a strip-shaped body such as a moving steel plate, images a screen on which the reflected light of the illumination light reflected on the surface of the strip-shaped body is projected, and analyses the captured image to measure the surface roughness distribution of the strip-shaped body. As shown in FIG. 1, the shape measurement apparatus 10 is composed of a screen image acquisition apparatus 100 and an arithmetic processing apparatus 200.

(1-1. Screen Image Acquisition Apparatus)

The screen image acquisition apparatus 100 successively captures images of the surface of a strip-shaped body moving on the conveyance line along the longitudinal direction of the strip-shaped body (that is, the movement direction), and outputs the obtained captured images to the arithmetic processing apparatus 200. As shown in FIG. 1, the screen image acquisition apparatus 100 includes a linear light source 101, a screen 103, and an imaging unit 105. The linear light source 101 applies linear illumination light to the surface of a strip-shaped body such as a moving steel plate. On the screen 103, the reflected light of illumination light that is generated by the linear illumination light applied from the linear light source 101 being reflected on the surface of the strip-shaped body is projected. The imaging unit 105 images the screen 103, and acquires a captured image that includes the reflected light of illumination light projected on the screen 103 as a screen image.

The linear light source 101, the screen 103, and the imaging unit 105 constituting the screen image acquisition apparatus 100 are, for example as shown in FIG. 2 to FIG. 4, installed above a line on which a strip-shaped body S is conveyed.

The linear light source 101 applies linear light to the surface of the strip-shaped body S moving on the conveyance line, the linear light extending in the width direction of the strip-shaped body S, from the upstream side or the downstream side in the movement direction of the strip-shaped body S (Y direction). The linear light source 101 like this may be configured by, for example, combining a light source unit such as a continuous wave (CW) laser light source that makes continuous oscillation, a super luminescent diode (SLD) light source, or a light emitting diode (LED) light source and a lens unit such as a rod lens. For the linear light source 101, the light emitted from the light source unit is spread in a circular sectorial plane toward the surface of the strip-shaped body S by the lens unit. Thus, the light applied from the linear light source 101 to the surface of the strip-shaped body S forms a linear shape. In the present invention, it is sufficient that the linear light source 101 be a light source of which the emitted light spreads in a circular sectorial form, and the lens unit may also use a lens other than a rod lens, such as a cylindrical lens or a Powell lens.

In the present invention, it is desirable that the linear light source 101 have a spectral half-width of 20 nm or more in order to avoid the influence of speckles. In addition, the angle of incidence of linear light applied from the linear light source 101 with respect to the surface of the strip-shaped body S is decided in accordance with target surface roughness of the surface of the strip-shaped body S. Note that detailed description about the setting of the linear light source 101 will be given later.

As shown in FIG. 2, the screen 103 is provided in a position facing the linear light source 101, and the reflected light of linear light reflected by the surface of the strip-shaped body S is projected on the screen 103. The breadth of the screen 103 has a width that makes it possible to project reflected light spanning the entire width of the strip-shaped body S, in accordance with the angle of spread of linear light and the projection distance to the screen. The height of the screen 103 is set so that reflected light is present on the projection surface of the screen 103 even when the projection position of reflected light is changed due to the shape of the strip-shaped body S, vibration occurring in association with the movement of the strip-shaped body S, a change in the thickness of the strip-shaped body S, etc.

As shown in FIG. 2, the imaging unit 105 is provided in a position facing the screen 103 and allowing the screen 103 to be imaged. An area camera is used as the imaging unit 105. The area camera includes a lens having a prescribed focal distance and an imaging element such as a charge-coupled device (CCD) or a complementary metal oxide semiconductor (CMOS). The imaging unit 105 images the projection surface 103a of the screen 103 on which the reflected light of linear light from the surface of the strip-shaped body S is projected, and generates a captured image. The reflected light of linear light from the surface of the strip-shaped body S projected on the projection surface 103a of the screen 103 may be referred to as a screen image.

In the imaging unit 105, the area to be imaged is adjusted in advance with reference to operation data in the past etc. so that the reflected light of linear light projected on the screen 103 is included in the visual field, and setting is made so that the projection surface of the screen 103 is imaged under the same imaging conditions. Here, an x-y-z coordinate system fixed to the imaging unit 105 like that shown in FIG. 3 and FIG. 4 is defined. In the coordinate system, the width direction of the imaging visual field of the imaging unit 105 is defined as the x-axis direction, the optical axis direction of the imaging unit 105 is defined as the y-axis direction, and the height direction of the imaging visual field of the imaging unit 105 is defined as the z-axis direction.

As shown in FIG. 3 and FIG. 4, the screen 103 is placed such that the normal vector of the projection surface expressed by the x-y-z coordinate system does not have an x-component (in other words, the value of the x-component is zero). That is, the positional relationship mentioned above may be satisfied in a state where, as shown by the solid line in the planar view shown in FIG. 3, the optical axis direction of the imaging unit 105 (the y-axis) and the movement direction of the strip-shaped body S (the Y-axis) are parallel. Alternatively, as shown by the alternate long and two short dashes line in FIG. 3, a state where the screen 103 and the imaging unit 105 are rotated around the z-axis from the state shown by the solid line while satisfying the positional relationship mentioned above is possible. Thereby, the image resolution along the width direction can be equalized in the visual field of the imaging unit 105.

Since it is sufficient that the image resolution along the width direction be equalized, the positional relationship between the screen 103 and the imaging unit 105 may be, for example as shown by the solid line in the side view shown in FIG. 4, a positional relationship in which the optical axis C of the imaging unit 105 is orthogonal to the projection surface 103a of the screen 103 in a state where the optical axis direction of the imaging unit 105 (the y-axis) and the movement direction of the strip-shaped body S (the Y-axis) are parallel. Alternatively, as shown by the alternate long and two short dashes line in FIG. 4, a state where the screen 103 and the imaging unit 105 are rotated around the x-axis from the state shown by the solid line while satisfying the positional relationship mentioned above is possible. Thereby, the image resolution along the width direction can be equalized in the visual field of the imaging unit 105. Further, in FIG. 4, since the image resolution along the width direction is equalized, either one of the screen 103 and the imaging unit 105 may be placed in the position shown by the solid line, and the other may be placed in the position shown by the alternate long and two short dashes line.

The captured image acquired by the imaging unit 105 thus installed is, for example as shown in FIG. 5, an image in which the reflected light of linear light (that is, the screen image) 55 appears in the size of the captured image 50 of a full frame. The imaging unit 105 outputs the acquired captured image to the arithmetic processing apparatus 200.

The screen image acquisition apparatus 100 described above may be controlled by, for example, the arithmetic processing apparatus 200. In general, the conveyance line that conveys the strip-shaped body S, which is the measurement object, is provided with a pulse logic generator (PLG, a pulse-type speed detector) or the like in order to detect the moving speed of the strip-shaped body S, for example. Thus, on the basis of a PLG signal of one pulse inputted from the PLG, the arithmetic processing apparatus 200 transmits a control signal to the imaging unit 105 of the screen image acquisition apparatus 100 at regular intervals, and can cause the imaging unit 105 to work, with the control signal as the imaging timing. Thus, the reflected light of linear light projected on the screen 103 is imaged every time the strip-shaped body S moves a prescribed distance, and a captured image can be acquired at regular intervals.

(1-2. Arithmetic Processing Apparatus)

The arithmetic processing apparatus 200 analyzes the captured image acquired by the screen image acquisition apparatus 100, and acquires surface roughness distribution of the strip-shaped body S. As shown in FIG. 1, the arithmetic processing apparatus 200 includes an image analysis unit 210, a surface roughness distribution acquisition unit 220, a determination unit 230, an output unit 240, and a storage unit 250.

On the basis of the captured image acquired by the imaging unit 105 of the screen image acquisition apparatus 100, the image analysis unit 210 acquires the width distribution of a light strip of the reflected light of the linear light applied to the strip-shaped body S included in the captured image (the screen image). The image analysis unit 210 is configured with, for example, a central processing unit (CPU), a read-only memory (ROM), a random access memory (RAM), a communication device, etc. In the shape measurement apparatus 10 according to the present embodiment, surface roughness distribution of the strip-shaped body S is acquired on the basis of the width distribution of the light strip. The width distribution of the light strip can be acquired by the image analysis of the captured image. Here, the "width distribution" of a light strip refers to a width (e.g., half-width) of the light strip of the screen image in a Z direction at each X coordinate.

On the basis of luminance values of the pixels of the captured image, the image analysis unit 210 extracts a pixel area of a preset threshold or more, thereby specifying the reflected light of the linear light applied to the strip-shaped body S included in the captured image (the light strip of the screen image). Then, the image analysis unit 210 acquires luminance distribution of the area specified as the light strip of the screen image, that is, a luminance profile of the screen image in the Z direction at each X coordinate. Furthermore, the image analysis unit 210 acquires width distribution of the light strip from the luminance profile of the screen image in the Z direction at each X coordinate, and outputs the width distribution to the surface roughness distribution acquisition unit 220.

The surface roughness distribution acquisition unit 220 acquires, from the width distribution of the light strip input from the image analysis unit 210, that is, the width of the light strip of the screen image in the Z direction at each X coordinate, roughness at each corresponding X coordinate on the steel plate, that is, surface roughness distribution of the strip-shaped body S. The surface roughness distribution acquisition unit 220 is configured with, for example, a CPU, a ROM, a RAM, a communication device, etc. The surface roughness distribution acquisition unit 220 outputs the acquired surface roughness distribution of the strip-shaped body S to the determination unit 230 and the output unit 240.

The determination unit 230 determines whether the surface of the strip-shaped body S has the target surface roughness, on the basis of the surface roughness distribution of the strip-shaped body S acquired by the surface roughness distribution acquisition unit 220. For example, the determination unit 230 acquires the target surface roughness to be achieved in the strip-shaped body S, which is defined in advance in the storage unit 250 described later, and determines whether the target surface roughness is achieved from the surface roughness distribution acquired by the surface roughness distribution acquisition unit 220. The determination unit 230 outputs a determination result to the output unit 240. The determination unit 230 like this is configured with, for example, a CPU, a ROM, a RAM, a communication device, etc.

The output unit 240 outputs the surface roughness distribution of the strip-shaped body S acquired by the surface roughness distribution acquisition unit 220, or the determination result of the determination unit 230 to a display device, a storage device, and other devices (all of these not illustrated). The output unit 240 is configured with, for example, a CPU, a ROM, a RAM, a communication device, etc.

The storage unit 250 is an example of the storage device included in the arithmetic processing apparatus 200, and is configured with, for example, a ROM, a RAM, a storage device, etc. For example, the storage unit 250 stores information needed for acquiring surface roughness distribution, such as a setting of the angle of incidence of the linear light source 101 corresponding to the target surface roughness of the surface of the strip-shaped body S, and the relationship between surface roughness and a width of the light strip of the screen image at each angle of incidence. In addition, the storage unit 250 stores the target surface roughness used when the determination unit 230 determines whether the surface of the strip-shaped body S has the target surface roughness. The target surface roughness changes depending on steel types, surface finish, or the like; hence, target surface roughness corresponding to each steel type, surface finish, or the like may be stored.

The arithmetic processing apparatus 200 according to the present embodiment may be configured to be capable of controlling the imaging processing that is performed by the screen image acquisition apparatus 100 and that captures the screen image, which is the reflected light of linear light on the surface of the strip-shaped body S. In this case, the arithmetic processing apparatus 200 may include, for example, an imaging control unit (not illustrated) that performs the control of the light emission of the linear light source 101, the control of the imaging of the imaging unit 105, etc. The imaging control unit is configured with, for example, a CPU, a ROM, a RAM, a communication device, etc.

(2. Shape Measurement Method)

A shape measurement method that measures surface roughness distribution of the strip-shaped body S using the shape measurement apparatus 10 described above will now be described in detail.

(2-1. Relationship Between Surface Roughness and Angle of Incidence of Linear Light Source)

A shape measurement method according to the present embodiment can also be referred to as a surface roughness measurement method that measures surface roughness distribution of the strip-shaped body S, and is a method suitable for measuring surface roughness of a steel plate or the like whose surface roughness is required to be managed. For example, a cold-rolled steel plate can be subjected to measurement of surface roughness on the exit side of a continuous annealing line on which the steel plate is passed after cold rolling, and a surface-treated steel plate, such as a galvanized steel plate, can be subjected to measurement of surface roughness on the exit side of a plating line on which the steel plate is passed after cold rolling.

Here, target surface roughness differs depending on a usage purpose of a steel plate. For example, in regard to a cold-rolled steel plate, target surface roughness is large when dull finish is performed as surface finish to provide a matt surface, and target surface roughness is small when bright finish is performed to provide a glossy surface. Specifically, in the case where root mean square (RMS) roughness Rq is used as an indicator of surface roughness, for example, the target surface roughness (Rq) of the cold-rolled steel plate is set to approximately 0.1 µm to several micrometers. The present inventors have found that there is an optimum angle of incidence of linear light in measurement of surface roughness, according to the difference in target surface roughness.

Figure 6:
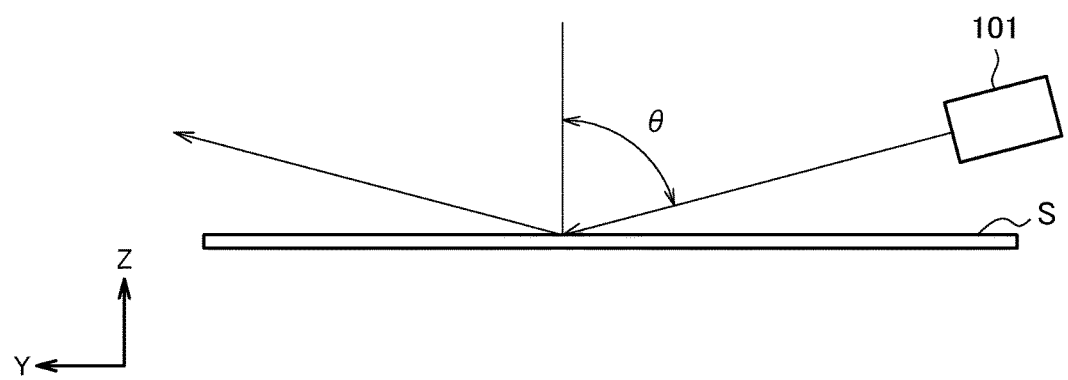
FIG. 6 is an explanatory diagram describing an angle of incidence on a strip-shaped body.

An angle of incidence θ of linear light emitted from the linear light source 101 on the strip-shaped body S refers to an inclination angle of the linear light with respect to a normal to the surface of the strip-shaped body S, as shown in FIG. 6. An optimum angle of incidence of the linear light, which is optimum in measuring surface roughness, is an angle of incidence allowing a light strip suitable for measurement of surface roughness to be projected on a screen. The "light strip suitable for measurement of surface roughness" refers to a light strip in the following case: luminance of a light strip of the reflected light of the linear light projected on the screen can be distinguished from luminance of texture on which the reflected light is projected in a portion not irradiated with the linear light on the surface of the strip-shaped body S, and the light strip has as large a width as possible.

The measurement of the surface roughness of the strip-shaped body S according to the present embodiment uses the principle of the optical lever, and is performed by acquiring a width and luminance of a screen image (light strip) in a captured image that is obtained by imaging the screen on which the reflected light on the surface of the strip-shaped body S is projected. A line width of the linear light emitted from the linear light source 101 is as small as approximately 0.1 mm until the linear light strikes the surface of the strip-shaped body S, but the linear light appears as a light strip having a prescribed width on the surface of the strip-shaped body S because it is applied to the surface of the strip-shaped body S diagonally, and when the reflected light reflected on the surface of the strip-shaped body S is projected on the screen, the light strip projected on the screen has a wider width. In the present embodiment, the angle of incidence of the linear light source 101 of the screen image acquisition apparatus 100 is set in a manner that the light strip that appears as a screen image as described above is suitable for measurement of surface roughness.

In the case where the angle of incidence θ of the linear light is not appropriately set, the reflected light of the linear light reflected on the surface of the strip-shaped body S is not properly projected on the screen 103. For example, when the angle of incidence θ is too large, the light strip of the reflected light projected on the screen 103 has a narrow width. In the shape measurement method according to the present embodiment, since surface roughness is specified on the basis of the width of the light strip of the reflected light, when the light strip of the reflected light in a normal case (i.e., in a case where the surface roughness is the target surface roughness) has a narrow width like a line, it is difficult to detect a slight change in surface roughness. In particular, as will be described later, in the case where the angle of incidence θ of the linear light is fixed, smaller surface roughness of the strip-shaped body S results in a narrower width of the light strip; hence, it is difficult to detect a change in surface roughness in the case where surface roughness is smaller than the target surface roughness. Therefore, the setting of the angle of incidence θ of the linear light is important.

Figure 7:
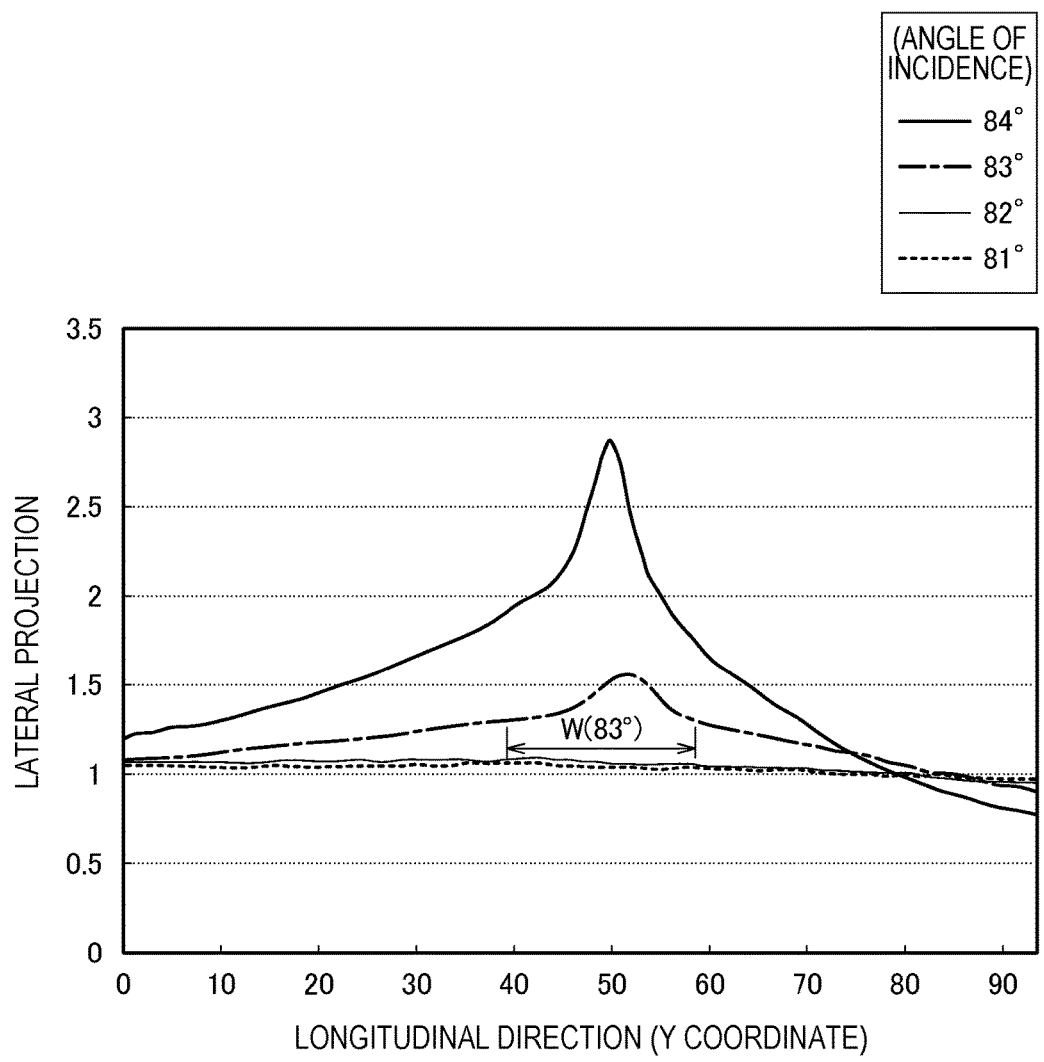
FIG. 7 is a graph showing, as lateral projection, an integrated value of luminance at each position in the longitudinal direction of the strip-shaped body, in regard to a steel plate A.
Figure 8:
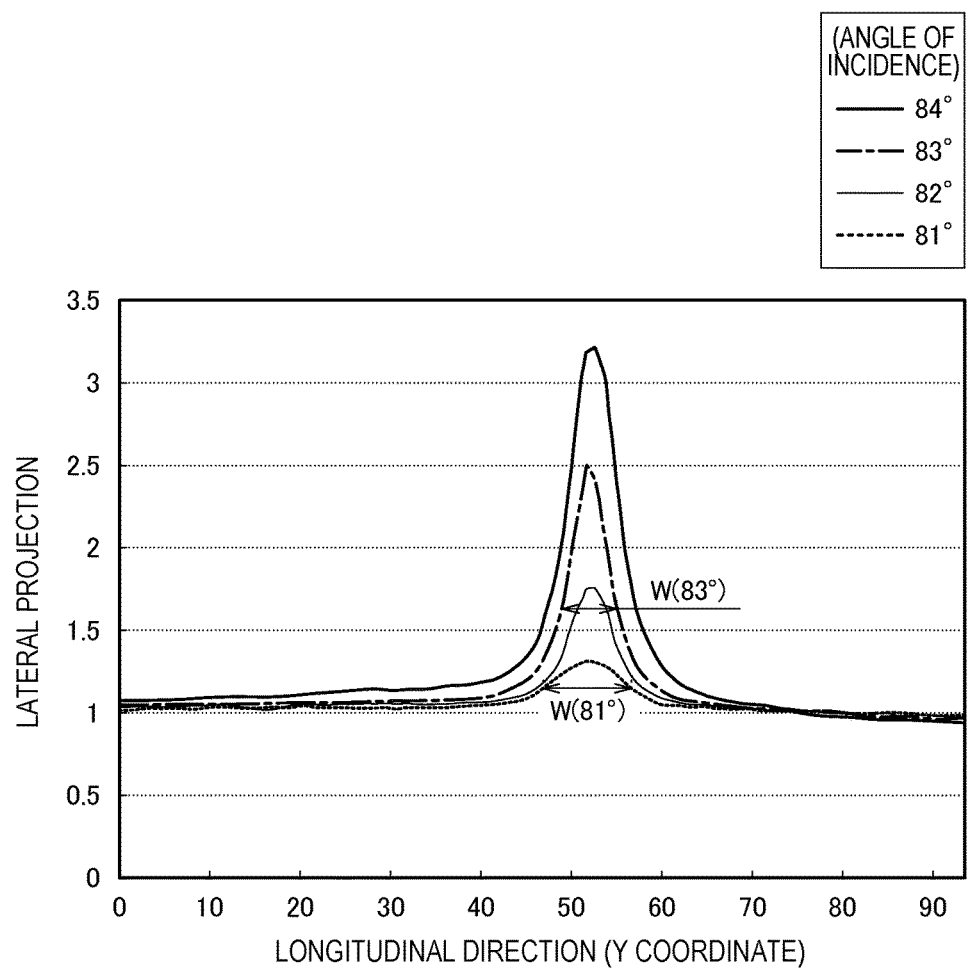
FIG. 8 is a graph showing, as lateral projection, an integrated value of luminance at each position in the longitudinal direction of the strip-shaped body, in regard to a steel plate B.

As an example, in regard to two types of steel plates that differ in surface roughness, a steel plate A with a target surface roughness (Rq) of 1.3 μm and a steel plate B with a target surface roughness of 0.5 μm, the optimum angle of incidence of the linear light in measuring surface roughness was studied. FIGS. 7 and 8 show results of the study. FIG. 7 is a graph showing, as lateral projection, an integrated value of luminance at each position in the longitudinal direction of the strip-shaped body S, in regard to the steel plate A. FIG. 8 is a graph showing, as lateral projection, an integrated value of luminance at each position in the longitudinal direction of the strip-shaped body S, in regard to the steel plate B. Here, the angle of incidence θ of the linear light was changed by 1° in a range of 81° to 84° in each graph, and a change in luminance at each angle of incidence was studied. Note that in regard to the linear light emitted from the linear light source 101, a line width until the linear light strikes the surface of the strip-shaped body S was set to 0.1 mm. As the luminance along the vertical axis shown as the lateral projection in FIGS. 7 and 8, normalized values are shown with luminance of a texture portion set at 1.

A half-width of a peak value of projection luminance at each position in the longitudinal direction shown in the lateral projection (i.e., a distance between two points at a position of half the peak value (full width at half maximum)) was taken as the width of the light strip, and an angle of incidence at which a light strip suitable for measurement of surface roughness is obtained was studied. For the steel plate A, a light strip suitable for measurement of surface roughness was projected on the screen when the angle of incidence was 83°. Note that the half-width (i.e., the width of the light strip) $W_{(83°)}$ was 2.4 mm. On the other hand, for the steel plate B, a light strip suitable for measurement of surface roughness was projected on the screen when the angle of incidence was 81° to 83°. Note that the half-width (i.e., the width of the light strip) $W_{(81°)}$ was 0.9 mm, and $W_{(83°)}$ was 0.5 mm. Here, the "light strip suitable for measurement" refers to a light strip having a width that allows detection of a change in the case where the surface roughness falls outside the target surface roughness. More specifically, the "light strip suitable for measurement" refers to a light strip that is significantly thicker than the thinnest width when the angle of incidence θ is changed (for example, 20% or more thicker than the thinnest width) and significantly thinner than a critical thickness recognizable as a light strip (for example, 20% or more thinner than the thickest width).

As described above, the angle of incidence θ of the linear light source 101 at which a light strip suitable for measurement of surface roughness is obtained differs depending on the target surface roughness. For example, the angle of incidence θ is set to be relatively small for a steel plate with small surface roughness, like a glossy steel plate subjected to bright finish. On the other hand, for example, the angle of incidence θ is set to be relatively large for a steel plate with large surface roughness, such as a steel plate after pickling, or a tin plate subjected to matte finish.

In addition, it has been found that the width of the light strip of the reflected light projected on the screen changes in accordance with a difference in surface roughness, and according to FIGS. 7 and 8, smaller surface roughness results in a smaller width of the light strip. For example, when the angle of incidence of the linear light source 101 was fixed at 83°, the half-width of the light strip (i.e., the width of the light strip) $W_{(83°)}$ when the steel plate A was measured was 2.4 mm, whereas the half-width of the light strip (i.e., the width of the light strip) $W_{(83°)}$ when the steel plate B was measured was 0.5 mm. Thus, when the angle of incidence of the linear light is the same, smaller surface roughness results in a smaller width of the light strip.

Figure 9:
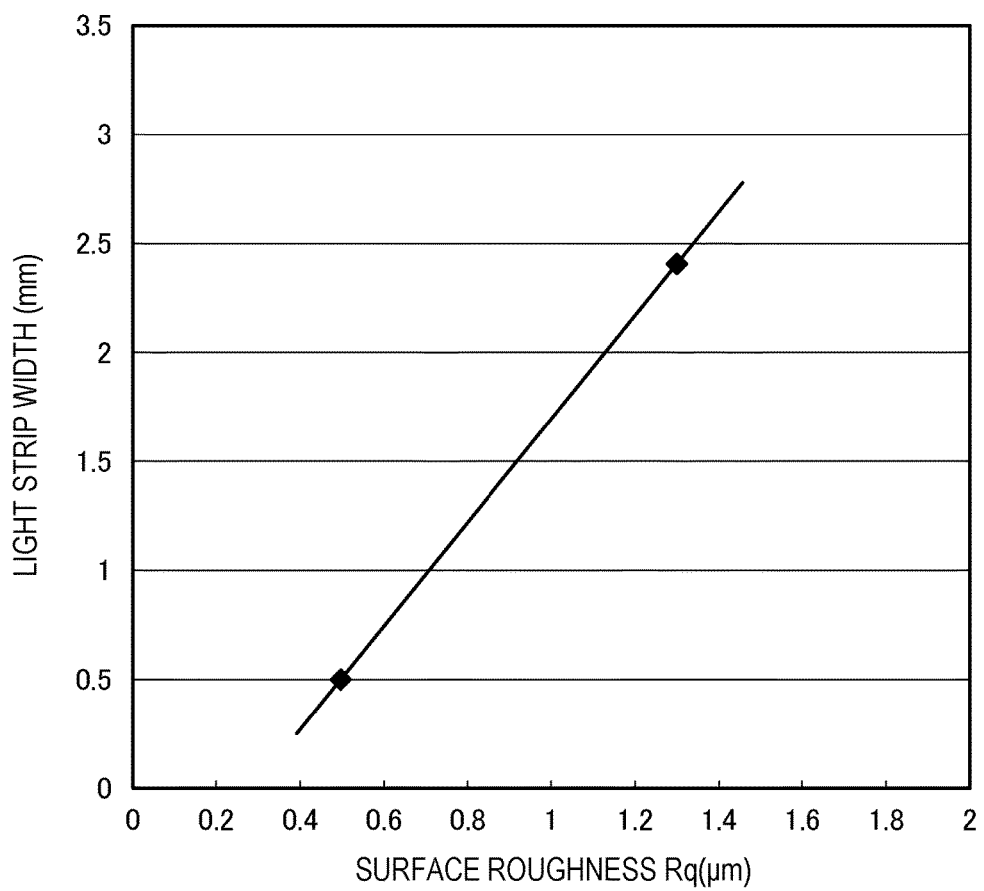
FIG. 9 is an explanatory diagram showing an example of correlation between surface roughness of the strip-shaped body and a width of a light strip at a certain angle of incidence.

This correlation between the surface roughness Rq of the strip-shaped body S and the width of the light strip (i.e., the width of the light strip changes in accordance with a difference in surface roughness, and smaller surface roughness results in a smaller width of the light strip) can be expressed as shown in FIG. 9, for example. FIG. 9 expresses the relationship between the surface roughness Rq of the strip-shaped body S and the width of the light strip that appears on the screen when the angle of incidence of the light strip linear light is set to 83°, in regard to the steel plate A and the steel plate B. If the target surface roughness (Rq) is in a range of approximately 0.5 to 1.3 μm corresponding to the steel plate B and the steel plate A, a large error is not caused by approximation as a proportional relationship as shown in FIG. 9. When such a correlation relationship is used, for example, surface roughness of a position at which the linear light is applied to the strip-shaped body S can be specified by fixing the angle of incidence of the linear light and acquiring the width of the light strip that appears on the screen.

Figure 10:
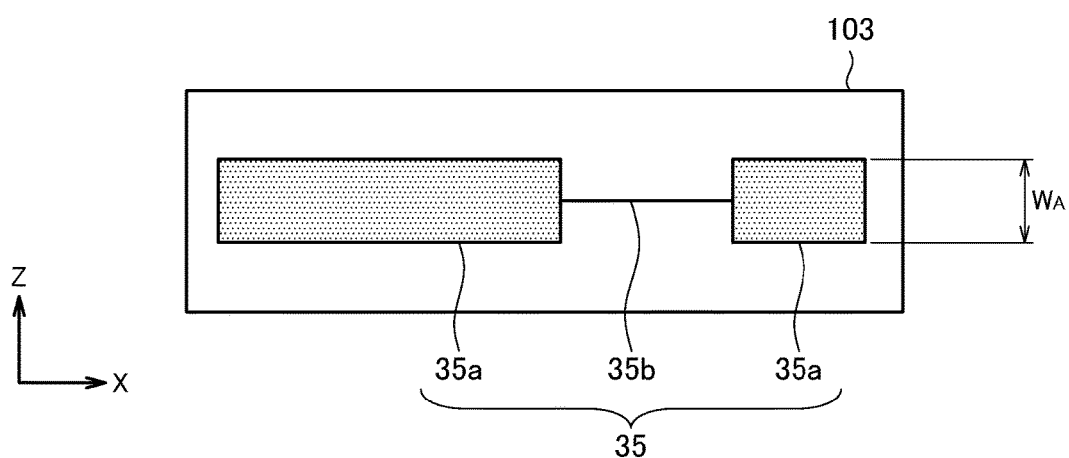
FIG. 10 is an explanatory diagram showing an example of a screen image projected on a projection surface of the screen.

As a specific example, assume that the reflected light of the linear light applied to the strip-shaped body S appears on the projection surface of the screen 103 as a screen image 35 as shown in FIG. 10. Here, in the case where the linear light source 101 is set at an angle of incidence allowing the light strip that appears on the screen 103 to have a light strip width $W_A$ when the surface roughness of the strip-shaped body S is the target surface roughness, the target surface roughness is found to be achieved in an area 35a (hereinafter also referred to as "normal area") of the screen image 35.

On the other hand, a narrow-width area 35b in which the width of the light strip is smaller than the light strip width $W_A$ is found to be an area in which the surface roughness is smaller than the target surface roughness, being an abnormal part in terms of surface roughness, according to the relationship between the surface roughness and the width of the light strip. The screen image as shown in FIG. 10 is observed in the case where, in rolling of a steel plate, for example, an area in which rolling oil has adhered to the surface of the steel plate in a large amount occurs on the surface of the steel plate due to a large amount of drawing of rolling oil to the steel plate. This is because, since the area in which rolling oil has adhered in a large amount has smaller surface roughness than other areas, the width of the light strip is narrower than that of the normal area 35a in which the target surface roughness is achieved, as in the narrow-width area 35*b* in FIG. 10. Alternatively, a similar screen image is obtained also in the case where abrasion partially occurs on a rolling mill roll.

Figure 11:
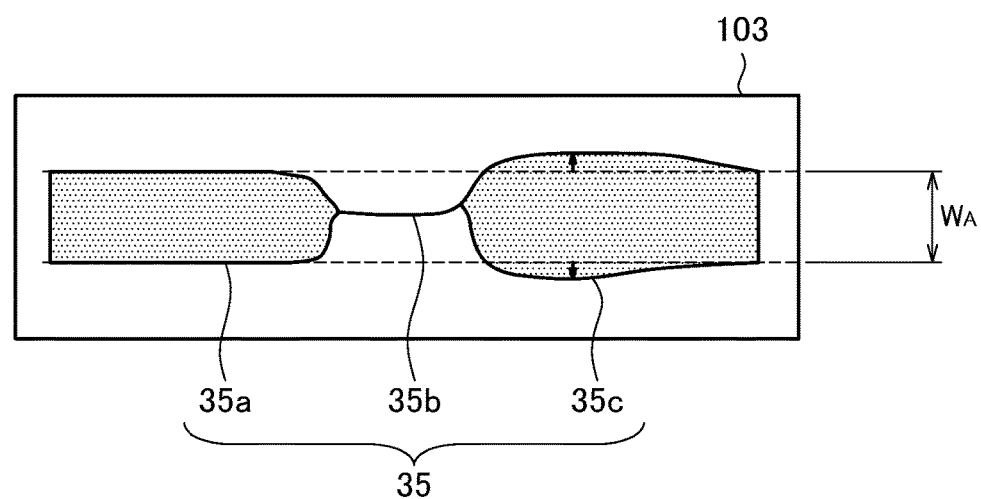
FIG. 11 is an explanatory diagram showing another example of a screen image projected on the projection surface of the screen.

Note that, in addition to the case where the narrow-width area 35*b* narrower than the normal area 35*a* with the light strip width $W_A$ in which the surface roughness is the target surface roughness appears as in the screen image 35 shown in FIG. 10, there also is a case where a wide-width area 35*c* with a width wider than the light strip width $W_A$ of the normal area 35*a* appears in the screen image 35 as shown in FIG. 11, for example. The wide-width area 35*c* is an area in which the surface roughness is larger than the target surface roughness, and can be determined as an abnormal part like the narrow-width area 35*b*.

As described above, for example, a laser light source, a SLD light source, a LED light source, or the like can be used as the linear light source 101; however, in the case where a light source having an extremely small spectral half-width, like a laser light source, is used, noise appears as spots called speckles around a screen image, which may lead to a decrease in measurement precision of a light strip width. In order to suppress a decrease in measurement precision due to such speckles, it is desirable that the linear light source have a spectral half-width of 20 nm or more.

(2-2. Processing Flow)

Figure 12:
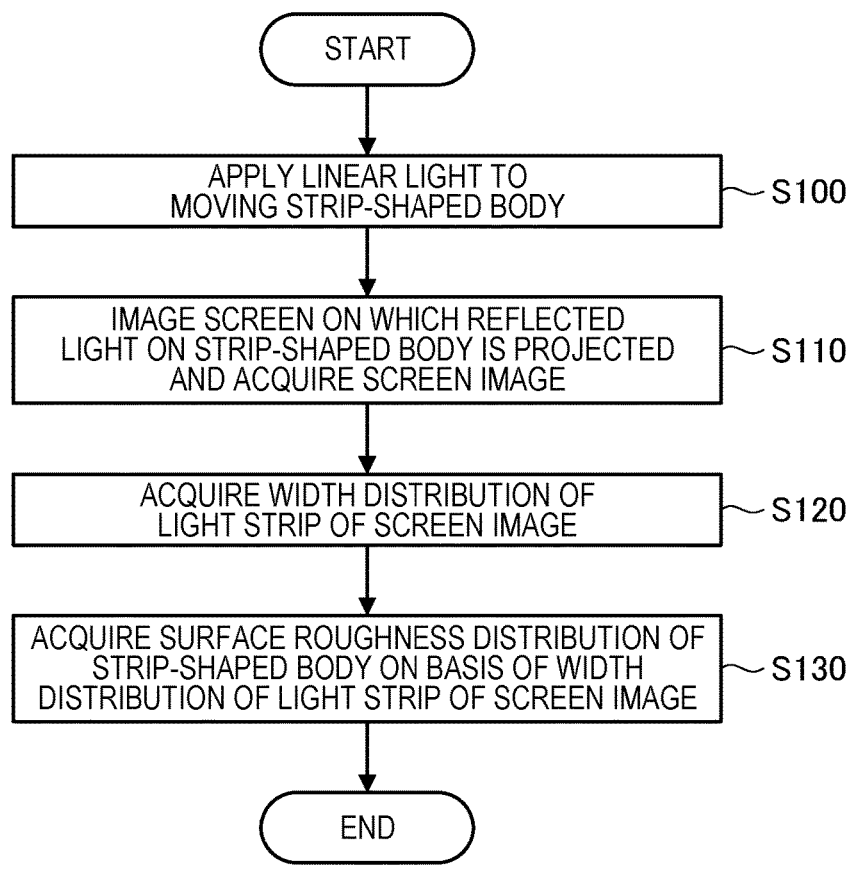
FIG. 12 is a flow chart showing a shape measurement method according to the embodiment.

A shape measurement method that measures surface roughness distribution of the strip-shaped body S according to an embodiment of the present invention is described on the basis of FIG. 12. FIG. 12 is a flow chart showing the shape measurement method according to the present embodiment.

In the shape measurement method executed using the screen image acquisition apparatus 100 according to the present embodiment, first, linear light is applied from the linear light source 101 to the surface of the strip-shaped body S moving on the conveyance line as shown in FIG. 2 (S100). When light is emitted from the linear light source 101, the surface of the strip-shaped body S is irradiated with linear light. Then, the reflected light of the linear light reflected on the surface of the strip-shaped body S is projected as the screen image 35 on the projection surface 103*a* of the screen 103.

Next, the imaging unit 105 images the screen 103 on which the reflected light of the linear light reflected on the surface of the strip-shaped body S is projected, and acquires a captured image including the screen image 35 (S110). Here, the angle of incidence of the linear light source 101 is set in a manner that the screen image 35 projected on the screen 103 has a light strip width suitable for measurement of surface roughness, when the surface roughness of an area irradiated with the linear light is the target surface roughness. At each angle of incidence of the linear light source 101, the relationship between the surface roughness of the area irradiated with the linear light and the light strip width of the screen image is obtained in advance by measurement; thus, the light strip width of the screen image when the surface roughness of the area irradiated with the linear light is the target surface roughness can be specified. Therefore, in the case where the surface roughness of a certain area of the strip-shaped body S falls outside the target surface roughness, an area having a width different from the light strip width corresponding to the target surface roughness appears as shown in FIGS. 10 and 11. The shape measurement method according to the present embodiment uses such a characteristic to acquire the surface roughness distribution of the strip-shaped body S. In step S110, the screen 103 is imaged, and a captured image including the screen image 35 is acquired, as information for acquiring the surface roughness distribution of the strip-shaped body S. The imaging unit 105 outputs the acquired captured image to the arithmetic processing apparatus 200.

In the arithmetic processing apparatus 200, when the captured image is input from the imaging unit 105, the image analysis unit 210 acquires width distribution of the light strip of the screen image included in the captured image (S120). The image analysis unit 210 specifies the reflected light of the linear light applied to the strip-shaped body S included in the captured image (screen image) on the basis of luminance values of the pixels of the captured image. Then, the image analysis unit 210 acquires the width distribution of the light strip, taking an area specified as the screen image as the light strip of the reflected light, and outputs the width distribution to the surface roughness distribution acquisition unit 220.

Then, in the arithmetic processing apparatus 200, the surface roughness distribution acquisition unit 220 acquires surface roughness distribution of the strip-shaped body S on the basis of the width distribution of the light strip acquired in step S120 (S130). The surface roughness distribution may be expressed like the screen image 35 projected on the screen 103 as in FIG. 10, for example. The surface roughness distribution acquisition unit 220 may, for example, output the acquired surface roughness distribution to the determination unit 230. In this case, the determination unit 230 may determine whether there is an area in which the surface roughness is outside the target surface roughness on the surface of the strip-shaped body S, according to the surface roughness distribution, for example. Specifically, an allowable value may be set, for example, and the determination unit 230 may determine whether the surface roughness is outside a range of the target surface roughness±the allowable value. This makes it possible to confirm that a desired product is produced. The determination unit 230 may output the determination result to the output unit 240, for example, to notify an operator of the determination result.

As described above, the shape measurement method according to the present embodiment uses the principle of the optical lever, and acquires the surface roughness distribution of the strip-shaped body S according to the width and luminance of the light strip of the reflected light projected on the screen 103, the reflected light being the linear light applied along the width direction of the strip-shaped body S and specularly reflected. Using the principle of the optical lever can make the width of the light strip of the screen image larger than the width of the light strip of the linear light on the strip-shaped body S. Therefore, surface roughness of the strip-shaped body S in the width direction can be measured with high sensitivity, which makes it possible to detect minute roughness irregularity at high speed across the entire width on the entire surface of a measurement object.

(3. Hardware Configuration)

Figure 13:
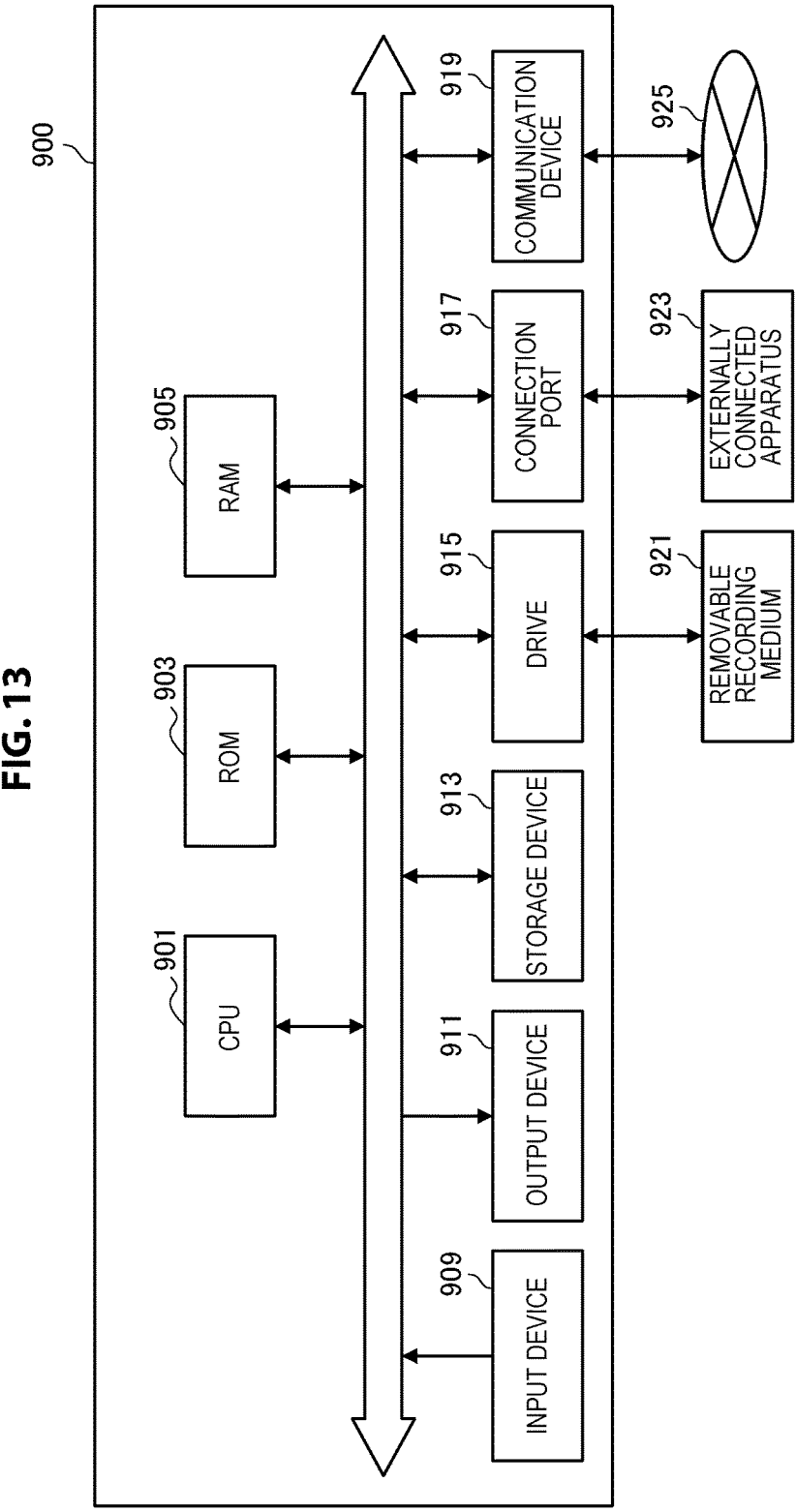
FIG. 13 is a block diagram for describing the hardware configuration of an information processing apparatus that serves as an arithmetic processing apparatus according to the embodiment.

The hardware configuration of the arithmetic processing apparatus 200 according to an embodiment of the present invention will be described in detail in FIG. 13. FIG. 13 is a block diagram for describing the hardware configuration of an information processing apparatus 900 that serves as the arithmetic processing apparatus 200 according to an embodiment of the present invention.

The information processing apparatus 900 that serves as the arithmetic processing apparatus 200 mainly includes a CPU 901, a ROM 903, and a RAM 905. Furthermore, the information processing apparatus 900 also includes a bus 907, an input device 909, an output device 911, a storage device 913, a drive 915, a connection port 917, and a communication device 919.

The CPU 901 serves as an arithmetic processing apparatus and a control device, and controls the overall operation or a part of the operation of the information processing apparatus 900 according to various programs recorded in the ROM 903, the RAM 905, the storage device 913, or a removable recording medium 921. The ROM 903 stores programs, operation parameters, and the like used by the CPU 901. The RAM 905 primarily stores programs that the CPU 901 uses and parameters and the like varying as appropriate during the execution of the programs. These are connected with each other via the bus 907 configured from an internal bus such as a CPU bus or the like.

The bus 907 is connected to the external bus such as a PCI (Peripheral Component Interconnect/Interface) bus via the bridge.

The input device 909 is an operation means operated by a user, such as a mouse, a keyboard, a touch panel, buttons, a switch and a lever. The input device 909 may be a remote control means (a so-called remote control) using, for example, infrared light or other radio waves, or may be an externally connected apparatus 923 such as a PDA conforming to the operation of the information processing apparatus 900. Furthermore, the input device 909 generates an input signal based on, for example, information which is input by a user with the above operation means, and is configured from an input control circuit for outputting the input signal to the CPU 901. The user of the information processing apparatus 900 can input various data to the information processing apparatus 900 and can instruct the information processing apparatus 900 to perform processing by operating this input device 909.

The output device 911 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, a mobile phone, a facsimile machine, and the like. For example, the output device 911 outputs a result obtained by various processes performed by the information processing apparatus 900. More specifically, the display device displays, in the form of texts or images, a result obtained by various processes performed by the information processing apparatus 900. On the other hand, the audio output device converts an audio signal such as reproduced audio data and sound data into an analog signal, and outputs the analog signal.

The storage device 913 is a device for storing data configured as an example of a storage unit of the information processing apparatus 900 and is used to store data. The storage device 913 is configured from, for example, a magnetic storage device such as a HDD (Hard Disk Drive), a semiconductor storage device, an optical storage device, or a magneto-optical storage device. This storage device 913 stores programs to be executed by the CPU 901, various data, and various data obtained from the outside.

The drive 915 is a reader/writer for recording medium, and is embedded in the information processing apparatus 900 or attached externally thereto. The drive 915 reads information recorded in the attached removable recording medium 921 such as a magnetic disk, an optical disk, a magneto-optical disk, or a semiconductor memory, and outputs the read information to the RAM 905. Furthermore, the drive 915 can write in the attached removable recording medium 921 such as a magnetic disk, an optical disk, a magneto-optical disk, or a semiconductor memory. The removable recording medium 921 is, for example, a CD medium, a DVD medium, or a Blu-ray (registered trademark) medium. The removable recording medium 921 may be a CompactFlash (CF; registered trademark), a flash memory, an SD memory card (Secure Digital Memory Card), or the like. Alternatively, the removable recording medium 921 may be, for example, an IC card (Integrated Circuit Card) equipped with a non-contact IC chip or an electronic device.

The connection port 917 is a port for allowing devices to directly connect to the information processing apparatus 900. Examples of the connection port 917 include a USB (Universal Serial Bus) port, an IEEE1394 port, a SCSI (Small Computer System Interface) port, an RS-232C port, and the like. By the externally connected apparatus 923 connecting to this connection port 917, the information processing apparatus 900 directly obtains various data from the externally connected apparatus 923 and provides various data to the externally connected apparatus 923.

The communication device 919 is a communication interface configured from, for example, a communication device for connecting to a communication network 925. The communication device 919 is, for example, a wired or wireless LAN (Local Area Network), Bluetooth (registered trademark), a communication card for WUSB (Wireless USB), or the like. Alternatively, the communication device 919 may be a router for optical communication, a router for ADSL (Asymmetric Digital Subscriber Line), a modem for various communications, or the like. This communication device 919 can transmit and receive signals and the like in accordance with a predetermined protocol such as TCP/IP on the Internet and with other communication devices, for example. The communication network 925 connected to the communication device 919 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the information processing apparatus 900 according to an embodiment of the present invention has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

The preferred embodiment(s) of the present invention has/have been described above with reference to the accompanying drawings, whilst the present invention is not limited to the above examples. A person skilled in the art may find various alterations and modifications within the scope of the appended claims, and it should be understood that they will naturally come under the technical scope of the present invention.

REFERENCE SIGNS LIST 10 shape measurement apparatus
100 screen image acquisition apparatus
101 linear light source
103 screen
105 imaging unit
200 arithmetic processing apparatus 210 image analysis unit
220 surface roughness distribution acquisition unit
230 determination unit
240 output unit
250 storage unit
S strip-shaped body

The invention claimed is:

1. A shape measurement apparatus comprising:
   a light source configured to irradiate a surface of a moving strip-shaped body with linear light at a prescribed angle of incidence from an upstream side or a downstream side in a movement direction of the strip-shaped body;
   a screen configured such that reflected light of the linear light on the surface of the strip-shaped body is projected on the screen;
   an area camera configured to image the reflected light of the linear light projected on the screen; and
   a central processing unit configured to acquire surface roughness distribution of the strip-shaped body to detect minute roughness irregularity on the basis of width distribution of a light strip of the reflected light of the linear light imaged by the area camera,
   wherein the prescribed angle of incidence is set in accordance with target surface roughness of the surface of the strip-shaped body, and
   wherein a width of the linear light is configured to be larger than the target surface roughness of the surface of the strip-shaped body.

2. The shape measurement apparatus according to claim 1, wherein a spectral half-width of the light source is 20 nm or more.

3. The shape measurement apparatus according to claim 1, wherein an angle of incidence of the light source is made larger for larger target surface roughness of the surface of the strip-shaped body.

4. The shape measurement apparatus according to claim 2, wherein an angle of incidence of the light source is made larger for larger target surface roughness of the surface of the strip-shaped body.

5. The shape measurement apparatus according to claim 1,
   wherein the central processing unit is further configured to:
      acquire, from luminance distribution of a light strip of reflected light of the strip-shaped body included in a captured image acquired by the area camera, width distribution of the light strip, and
      acquire the surface roughness distribution of the strip-shaped body on the basis of the width distribution of the light strip.

6. The shape measurement apparatus according to claim 5,
   wherein the central processing unit is further configured to:
      determine whether the surface of the strip-shaped body has the target surface roughness, on the basis of the surface roughness distribution.

7. The shape measurement apparatus according to claim 2,
   wherein the central processing unit is further configured to:
      acquire, from luminance distribution of a light strip of reflected light of the strip-shaped body included in a captured image acquired by the area camera, width distribution of the light strip, and
      acquire the surface roughness distribution of the strip-shaped body on the basis of the width distribution of the light strip.

8. The shape measurement apparatus according to claim 7,
   wherein the central processing unit is further configured to:
      determine whether the surface of the strip-shaped body has the target surface roughness, on the basis of the surface roughness distribution.

9. The shape measurement apparatus according to claim 3,
   wherein the central processing unit is further configured to:
      acquire, from luminance distribution of a light strip of reflected light of the strip-shaped body included in a captured image acquired by the area camera, width distribution of the light strip, and
      acquire the surface roughness distribution of the strip-shaped body on the basis of the width distribution of the light strip.

10. The shape measurement apparatus according to claim 9,
    wherein the central processing unit is further configured to:
       determine whether the surface of the strip-shaped body has the target surface roughness, on the basis of the surface roughness distribution.

11. The shape measurement apparatus according to claim 4,
    wherein the central processing unit is further configured to:
       acquire, from luminance distribution of a light strip of reflected light of the strip-shaped body included in a captured image acquired by the area camera, width distribution of the light strip, and
       acquire the surface roughness distribution of the strip-shaped body on the basis of the width distribution of the light strip.

12. The shape measurement apparatus according to claim 11,
    wherein the central processing unit is further configured to:
       determine whether the surface of the strip-shaped body has the target surface roughness, on the basis of the surface roughness distribution.

13. A shape measurement method comprising:
    a first step of using a light source to irradiate a surface of a moving strip-shaped body with linear light diagonally from an upstream side in a movement direction of the strip-shaped body, and using an area camera to image a screen on which reflected light of the linear light on the surface of the strip-shaped body is projected and acquiring a captured image in which a screen image that is reflected light of the strip-shaped body is included, the light source being installed to have an angle of incidence set in accordance with target surface roughness of the surface of the strip-shaped body so that a width of the linear light is larger than the target surface roughness of the surface of the strip-shaped body; and
    a second step of acquiring surface roughness distribution of the strip-shaped body to detect minute roughness irregularity on the basis of width distribution of a light strip of the reflected light of the linear light projected on the screen.

* * * * *

UNITED STATES PATENT AND TRADEMARK OFFICE
CERTIFICATE OF CORRECTION

PATENT NO. : 10,527,410 B2
APPLICATION NO. : 15/767081
DATED : January 7, 2020
INVENTOR(S) : Toshio Akagi et al.

Page 1 of 1

It is certified that error appears in the above-identified patent and that said Letters Patent is hereby corrected as shown below:

On the Title Page

<u>On page 2</u>
(56) References Cited:
FOREIGN PATENT DOCUMENTS:
Change "JP 2004-184397 A 5/2002" to --JP 2002-139447 A 5/2002--.

Signed and Sealed this
Third Day of March, 2020

Andrei Iancu
*Director of the United States Patent and Trademark Office*